United States Patent [19]
Arnoldy et al.

[11] Patent Number: 5,811,590
[45] Date of Patent: Sep. 22, 1998

[54] HYDROFORMYLATION PROCESS

[75] Inventors: Peter Arnoldy; Arnoldus Maria Iping, both of Amsterdam, Netherlands

[73] Assignee: Shell Oil Company, Houston, Tex.

[21] Appl. No.: 733,049

[22] Filed: Oct. 16, 1996

[30] Foreign Application Priority Data

Oct. 25, 1995 [EP] European Pat. Off. .............. 95202890

[51] Int. Cl.⁶ .................................................. C07C 45/00
[52] U.S. Cl. ............................................................ 568/451
[58] Field of Search .................................. 568/895, 900, 568/448, 451; 502/325, 339

[56] References Cited

U.S. PATENT DOCUMENTS 3,627,843 12/1971 Gianfranco et al. .
4,612,403 9/1986 Virnig .

FOREIGN PATENT DOCUMENTS 0220767 6/1987 European Pat. Off. .
2256641 12/1992 United Kingdom .
WO 95/05354 2/1995 WIPO ............................. C07C 29/16

OTHER PUBLICATIONS

International Search Report of 10 Dec. 1996.

*Primary Examiner*—Michael L. Shippen
*Assistant Examiner*—Karl J. Puttlitz, Jr.
*Attorney, Agent, or Firm*—Dennis V. Carmen

[57] ABSTRACT

A process is provided for the hydroformylation of ethylenically unsaturated compounds having at least 4 carbon atoms by reaction thereof with carbon monoxide and hydrogen in the presence of a solvent and a catalyst system obtainable by combining:

a) a source of Group VIII metal cations;
b) a source of anions; and
c) a source of phosphine ligands, wherein the solvent is a $C_1$ to $C_{10}$ alkane or alkene having two or more cyano groups attached.

8 Claims, No Drawings

HYDROFORMYLATION PROCESS

FIELD OF THE INVENTION

The invention relates to a process for the hydroformylation of ethylenically unsaturated compounds by reaction thereof with carbon monoxide and hydrogen in the presence of a catalyst and a solvent.

BACKGROUND OF THE INVENTION

The hydroformylation of ethylenically unsaturated compounds to form oxo-aldehydes and/or oxo-alcohols, hereinafter referred to as oxo-products, is of considerable industrial importance. The process has been in commercial operation for decades and over the years much development work has been done to optimise the reaction conditions, the catalyst system and the equipment. Although significant progress regarding the separation and reuse of the catalyst system has been made, it is felt that in some aspects further improvement of the process is still needed.

In International application WO 95/05354 a process is disclosed wherein a major part of the metallic component of the catalyst system is recovered upon cooling a single-phase liquid reaction medium comprising the reaction mixture and an aprotic solvent containing a strong polar group. Thus, a multiphase liquid reaction medium is formed comprising one phase in which a major part of the metallic component of the catalyst system is present and at least one further phase containing a major portion of the oxo-product.

The preferred solvent in WO 95/05354 is sulfolane. Sulfolane is particularly suitable in the production of higher ($C_{11}$+) oxo-alcohols, when cooling to about ambient temperature suffices to form the multiphase liquid reaction medium. Regrettably, when producing lower oxo-products more rigorous cooling or more solvent is needed to cause phase separation. It will be appreciated that this adversely affects the economy of the process. Furthermore, traces of sulfolane remaining in the product phase need to be removed in a separate step to provide an oxo-product that meets regulatory standards regarding the contents of sulfurous compounds. It is therefore desirable to find alternatives to sulfolane that perform in an alike manner, and that may be selected at will to suit the range of oxo-products produced in a process as discussed above. However, such is not an easy task, as the alternatives must: (i) be a fluid at all working conditions; (ii) be catalytically inert or promoting; (iii) be able to dissolve the catalyst under reaction and separation conditions, (iv) provide a single phase at reaction conditions and allow phase separation with lower oxo-products (e.g., $C_7$–$C_{11}$ range) and/or higher oxo-products (e.g., $C_{11}$–$C_{18}$ range) at separation conditions, and (v) be thermally and chemically stable.

SUMMARY OF THE INVENTION

Surprisingly, the inventors have found a class of compounds that allow phase separation without excessive cooling or use of large amounts thereof, and that meet these conditions. Accordingly, a process is provided for the hydroformylation of ethylenically unsaturated compounds having at least 4 carbon atoms by reaction thereof with carbon monoxide and hydrogen in the presence of a solvent and a catalyst system obtainable by combining:

a) a source of Group VIII metal cations;
b) a source of anions; and
c) a source of phosphine ligands, wherein the solvent is a $C_1$ to $C_{10}$ alkane or alkene having two or more cyano groups attached.

DETAILED DESCRIPTION OF THE INVENTION

Preferably, the solvent is a $C_1$ to $C_6$ alkane or alkene having two or more cyano groups attached. For instance, suitable solvents include dicyanomethane (malononitrile), 1,2-dicyanoethane (succinonitrile), 1,4-dicyanobutane (adiponitrile), 1,4-dicyano-2-butene (dihydromuconitrile), 1,5-dicyanopentane (pimelonitrile), 1,6-dicyanohexane (suberonitrile), 1,6-dicyanocyclohexane, and 1,2,4-tricyanobutane, etc. and mixtures thereof either or not with sulfolane.

When preparing the higher oxo-products, it is preferred to use a solvent in the higher carbon atom range, such as adiponitrile. Solvents in the lower carbon range, such as malonitrile, are preferred when preparing the lower oxo-products.

The hydroformylation process of the invention may be carried out in a homogeneous reaction medium using a dissolved catalyst system of adequate activity, whereby nevertheless the catalyst, without significant loss or decomposition thereof, can be readily recovered and reused if so desired.

Accordingly, the invention relates to a process for the hydroformylation of ethylenically unsaturated compounds having at least 4 carbon atoms by reaction thereof with carbon monoxide and hydrogen in a single-phase liquid reaction medium, in the presence of the aforementioned catalyst system, followed by effecting the formation of a multiphase liquid reaction medium, preferably by cooling the single-phase liquid reaction medium, comprising one phase in which a major part of the Group VIII metal cations of the catalyst system is present and at least one further phase containing a major portion of the hydroformylated product, wherein as solvent a $C_1$ to $C_{10}$ alkane or alkene having two or more cyano groups attached is used.

In this manner it is possible to ensure that a major portion of the metallic component of the catalyst system, i.e. more than 70% thereof, is present in the liquid phase containing the inert solvent, whereas more than 80% of the oxo-product is present in another phase, the oxo-product phase, from which it can be easily recovered by known techniques.

Using any of the solvents mentioned above, in combination with a well-selected oxo-product, the multiphase liquid medium can be readily formed when the temperature of the reaction mixture is decreased to close to ambient temperatures. If desired, the reaction medium can be cooled to lower temperatures, but for large-scale operation this is not considered of special advantage, in view of the additional provisions needed for cryogenic cooling.

Mixtures of solvents may also be used, for example a mixture of one of the aforementioned solvents with sulfolane or with a protic solvent, such as an alcohol. In the latter embodiment, the alcohol will separate into the oxo-product phase. Typically, an alcohol is selected which is identical or similar to the oxo-alcohol as obtained in the hydroformylation reaction. For ease of operation, preferably a single solvent, which is a $C_1$ to $C_{10}$ alkane or alkene having two or more cyano groups attached, is used.

The amount of solvent to be used in the process of the invention may vary considerably. For instance, the amount of solvent may vary from 3 to 50% by volume. Preferably, the multiphase liquid reaction medium is formed by cooling the single-phase liquid reaction medium to a temperature within the range of 0° to 50° C., more preferably within the range of 25° to 45° C. However, it is within the reach of those skilled in the art to establish in each case the degree of cooling and the optimal amount of solvent required for the formation of a multiphase liquid reaction medium. No specific pressure requirements or atmospheric conditions apply. The experimental results provided hereinafter are also indicative for the amount of solvent preferably to be used.

The ethylenically unsaturated compound used as starting material is preferably an olefin having from 4 to 24 carbon atoms per molecule, or a mixture thereof. It is believed that with ethylenically unsaturated compounds having only 2 or 3 carbon atoms per molecule, the formation of a multiphase liquid reaction medium, whereby the metallic component of the catalyst system is present in one phase and a major portion of the oxo-product in another phase, can not be easily effected.

The ethylenically unsaturated compound may comprise one or more double bonds per molecule. Preferred are internal olefins having from 6 to 14 carbon atoms, or mixtures thereof. Such olefin mixtures are commercially readily available as products of a process for the oligomerization of ethylene, followed by a double bond isomerization and disproportionation reaction. Typical examples are mixtures of linear internal $C_6$ to $C_8$ olefins, of linear internal $C_{11}$ to $C_{12}$ olefins, and of linear internal $C_{13}$ to $C_{14}$ olefins. However, also alpha-olefins having from 6 to 14 carbon atoms may be used, for instance in the presence of a Pt-based catalyst system.

Carbon monoxide and hydrogen may be supplied in equimolar or non-equimolar ratios, e.g. in a ratio within the range of 5:1 to 1:5, typically 3:1 to 1:3. Preferably they are supplied in a ratio within the range of 2:1 to 1:2.

In the present specification the metals of Group VIII are identified by their symbol as Fe, Co, Ni, Ru, Rh, Pd, Os, Ir and Pt. Preferred are the metals of the platinum group, i.e., Ni, Pd and Pt. Of these, palladium is most preferred. Examples of suitable metal sources are compounds such as salts of the metal and nitric acid, sulfuric acid, sulfonic acids, or carboxylic acids with up to 12 carbon atoms; metal complexes, e.g. with carbon monoxide or acetylacetonate; or the metal combined with a solid material such as an ion exchanger or carbon. Palladium(II) acetate and platinum(II) acetylacetonate are examples of preferred metal sources.

As component (b), any compound generating anions may be used. Such compounds may comprise acids or salts thereof; for example, any of the acids mentioned above, which may also participate in the salts of the Group VIII metals. The anions are preferably derived from strong acids, i.e., acids having a pKa value of less than 3, preferably less than 2 as measured in aqueous solution at 18° C. The anions derived from these acids are non-coordinating or weakly coordinating with the Group VIII metals. The stronger the acid, the less the anion coordinates with the Group VIII metal cation and the higher is the linearity of the hydroformylation product.

Typical examples of suitable anions are anions of phosphoric acid, sulfuric acid, sulfonic acids and halogenated carboxylic acids such as trifluoroacetic acid. Also, complex anions are suitable, such as the anions generated by a combination of a Lewis acid such as $BF_3$, $B(C_6F_5)_3$, $AlCl_3$, $SnF_2$, $Sn(CF_3SO_3)_2$, $SnCl_2$ or $GeCl_2$, with a protic acid, such as a sulfonic acid, e.g. $CF_3SO_3H$ or $CH_3SO_3H$ or a hydrohalogenic acid such as HF of HCl, or a combination of a Lewis acid with an alcohol. Examples of such complex anions are $BF_4-$, $SnCl_3-$, $[SnCl_2.CF_3SO_3]^-$ and $PF_6-$. The preferred anion source is trifluoromethanesulfonic acid.

The phosphine ligand is preferably a bidentate ligand of the formula

R1R2P—R—PR3R4 (I)

wherein R represents a bivalent organic bridging group containing from 1 to 4 atoms in the bridge, R1 and R2 together represent a bivalent substituted or non-substituted cyclic group whereby the two free valencies are linked to one P atom and R3 and R4 independently represent a substituted or non-substituted hydrocarbyl group, or together represent a bivalent substituted or non-substituted cyclic group whereby the two free valencies are linked to the other P atom.

In the organic bridging group, represented by R, typically all bridging groups are carbon atoms. Preferably the bridging group contains two carbon atoms in the bridge and is for example an ethylene group.

The bivalent (substituted) cyclic group, represented by $R^1$ together with $R^2$, in general comprises at least 5 ring atoms and preferably contains from 6 to 9 ring atoms. More preferably the cyclic group contains 8 ring atoms. Substituents, if any, are usually alkyl groups having from 1 to 4 carbon atoms. As a rule, all ring atoms are carbon atoms, but bivalent cyclic groups containing one or two heteroatoms in the ring, such as oxygen- or nitrogen, atoms are not precluded. Examples of suitable bivalent cyclic groups are 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

Preferred bivalent cyclic groups are selected from 1,4-cyclooctylene, 1,5-cyclooctylene, and methyl (di)substituted derivatives thereof.

Mixtures of ligands comprising different bivalent cyclic groups may be used as well, e.g. mixtures of ligands with 1,4-cyclooctylene and ligands with 1,5-cyclooctylene groups.

In the ligands of formula (I), $R^3$ and $R^4$ may independently represent various non-cyclic or cyclic groups, optionally substituted with substituents such as alkoxy groups with 1 to 4 carbon atoms, halogen atoms or ($C_1$ to $C_4$ alkyl)amino groups.

Examples are alkyl groups such as ethyl, isopropyl, sec-butyl and tert-butyl groups, cycloalkyl groups such as cyclopentyl and cyclohexyl groups, aryl groups such as phenyl and tolyl groups and bivalent groups such as a hexamethylene group. However, preferably $R^3$, together with $R^4$ represents a bivalent cyclic group, in particular the same group as the group represented by $R^1$ together with $R^2$, in which case the two free valencies of the bivalent cyclic group are, of course, linked to $M^2$, instead of $M^1$. Thus, preferred bidentate ligands of formula (I) are 1,2-bis(1,4-cyclooctylenephosphino)ethane, 1,2-bis(1,5-cyclooctylenephosphino)ethane and mixtures thereof, as well as the homologues having two methyl groups attached to one or each of the cyclooctylenephosphino groups.

For the preparation of the bidentate ligands, reference is made to known techniques, for example the method disclosed in GB-A-1,127,965.

The quantity in which the catalyst system is used, is not critical and may vary within wide limits. Usually amounts in the range of $10^{-8}$ to $10^{-1}$, preferably in the range of $10^{-7}$ to $10^{-2}$ mole atom of Group VIII metal per mole of ethylenically unsaturated compound are used. The amounts of the participants in the catalyst system are conveniently selected such that per mole atom of Group VIII metal from 0.5 to 6, preferably from 1 to 2 moles of bidentate ligand are used, and from 0.5 to 15, preferably from 1 to 8 moles of anion source or a complex anion source (i.e., component b) are used.

The hydroformylation can be suitably carried out at moderate reaction conditions. Hence temperatures in the range of 50° to 200° C. are recommended, preferred temperatures being in the range of 70° to 160° C. Reaction pressures in the range of 1 to 300 bar abs are suitable, but in the range of 5 to 100 bar abs are preferred. Lower or higher pressures may be selected, but are not considered particularly advantageous. Moreover, higher pressures require special equipment provisions.

The process of the invention is eminently suitable to be used for the preparation of alcohols from internal olefins at high rate, in particular by using a catalyst system as defined above, based on palladium.

Furthermore the process is very useful for the preparation of aldehydes having a high linearity, in particular by using a catalyst system as defined above, based on platinum as Group VIII metal.

The invention will be illustrated by the non-limiting examples, as described hereinafter.

COMPARATIVE EXAMPLES A AND B, AND EXAMPLE 1

Three experiments were carried out using respectively sulfolane (Comp. A), acetonitrile (Comp. B), and adiponitrile (Example 1) as solvent. These experiments were conducted in a 300 ml magnetically stirred autoclave ("Hastelloy", a trademark) at 105° C. and 50 bar abs (hydrogen gas/carbon monoxide ratio of 2:1 v/v). The autoclave was charged with 56 g of an internal $C_{11}$–$C_{12}$ olefin (40% $C_{11}$, 60% $C_{12}$, ex. SHELL), 49 g of 2-ethyl-hexanol, 0.8 g water, 1–2 g $C_{13}$ paraffin and an amount of solvent set out in the Table. The catalyst was obtained by combining palladium(II) acetate, diphosphine (90% isomeric pure 1,2-bis(1,5-cyclooctylenephosphino)ethane), trifluoromethanesulfonic acid and zinc chloride in a molar ratio of 1:1.4: (1.9–2.6):1.5. The Pd concentration in the reactor was 0.04% by weight on total contents.

The reaction was followed by means of GC. Typically, at virtual complete conversion (better than 99%) an overall alcohol yield of around 98% was observed. By-products are paraffin and, at incomplete conversion, aldehydes and heavy ends of the acetal type. Linearity (ratio n over n and branched in percent) was also determined by GC. Kinetic analysis provided pseudo first-order rate constants.

After a reaction period of 4 hours, during which no further hydrogen or carbon monoxide was supplied, the single-phase reaction mixture was cooled to ambient temperature. Two liquid layers were formed in case sulfolane and adiponitrile were employed. Palladium was detected visually in the solvent layer.

Additional details and analytical results are compiled in the Table following hereafter.

Further comparative tests involved dimethylsulfoxide, N,N-dimethylformamide, 2-pyrrolidone, N-methyl-2-pyrrolidone, 1,3-dimethyl-2-imidazolidinone, monoethyleneglycol, diethyleneglycol, monomethyl ether of diethyleneglycol, triethyleneglycol, 1,2-propyleneglycol, 1,4-butanediol, monoethanolamine, triethanolamine, anisole and tributylphosphineoxide, and glycerol. Albeit these solvents may be used in accordance with the teaching of WO 95/05354, either excessive cooling or large amounts of solvent are required, since in most cases no phase separation was observed at 25° C. for mixtures of 20% w solvent with 80% w $C_{12}$–$C_{13}$ oxo-product. Only when monoethyl glycol and glycerol were employed was phase separation observed. However, in these cases the catalytic performance was extremely low. These results prove that the presently-claimed class of solvents comprises the preferred substitutes for sulfolane.

TABLE

| Exp. No. | A | B | 1 |
|---|---|---|---|
| Solvent conc. | sulfolane | acetonitrile | adiponitrile |
| (% w/% vol) | 15.4/10 | 10.3/10 | 4.4/3.5 |
| Conv. 2h. (%) | 95 | 89 | 82 |
| Activity (H$^{-1}$) | 1.5 | 1.1 | 0.9 |
| Linearity (%) | 77 | 78 | 76 |
| Paraffin (% w) | 0.7 | 0.8 | 0.6 |
| Aldehyde (% w) | 0.8 | 0.9 | 2.5 |
| Alcohol (% w) | 88 | 96 | 83 |
| Heavy Ends (% w) | 10 | 2.4 | 14 |
| Phase separation | | | |
| at 20° C. | + | –* | + |
| at 105° C. | – | – | – |

*no phase separation at 25° C. when the concentration of acetonitrile is increased to 20% w.

We claim:
1. A process for the hydroformylation of ethylenically unsaturated compounds having at least 4 carbon atoms by reaction thereof with carbon monoxide and hydrogen in the presence of a solvent and a catalyst system obtained by combining:

a) a source of Group VIII cations;
  b) a source of anions; and
  c) a source of phosphine ligands, wherein the solvent comprises a $C_1$ to $C_{10}$ alkane having two or more cyano groups attached, or a $C_1$ to $C_{10}$ alkene having two or more cyano groups attached.

2. A process as claimed in claim 1, wherein the reaction is carried out in a single-phase liquid medium, followed by effecting the formation of a multiphase liquid reaction medium, by cooling the single-phase liquid medium, said multiphase liquid reaction medium comprising one phase in which a major part of the metallic component of the catalyst system is present and at least one further phase containing a major portion of the hydroformylated product.

3. A process as claimed in claim 2, wherein the solvent comprises dicyanomethane (malononitrile), 1,2-dicyanoethane (succinonitrile), 1,4-dicyanobutane (adiponitrile), 1,4-dicyano-2-butene (dihydromuconitrile), 1,5-dicyanopentane (pimelonitrile), 1,6-dicyanohexane (suberonitrile), or 1,2,4-tricyanobutane.

4. A process as claimed in claim 2, wherein component (a) of the catalyst system is based on a palladium or platinum compound.

5. A process as claimed in claim 4, wherein component (b) of the catalyst system is derived from an acid having a pKa value of less than 3, as measured in aqueous solution at 18° C.

6. A process as claimed in claim 5, wherein component (b) of the catalyst system is derived from an anion of phosphoric acid, sulfuric acid, sulfonic acids, halogenated carboxylic acids or is a complex anion.

7. A process as claimed in claim 5, wherein component (c) of the catalyst system comprises a bidentate ligand represented by the formula $$R^1R^2P\text{—}R\text{—}PR^3R^4 \tag{I}$$

wherein R represents a bivalent organic bridging group containing from 1 to 4 atoms in the bridge, $R^1$ and $R^2$ together represent a bivalent substituted or non-substituted cyclic group whereby the two free valencies are linked to one P atom, and $R^3$ and $R^4$ independently represent a substituted or non-substituted hydrocarbyl group, or together represent a bivalent substituted or non-substituted cyclic group whereby the two free valencies are linked to the other P atom.

8. A process as claimed in claim 7, wherein component (c) of the catalyst system is based on 1,2-bis(1,4-cyclooctylenephosphino)ethane, 1,2-bis(1,5-cyclo-octylenephosphino)ethane or mixtures thereof.

* * * * *